US00PP11263P

United States Patent [19]

Marciel et al.

[11] Patent Number: Plant 11,263

[45] Date of Patent: Mar. 7, 2000

[54] FLORIBUNDA ROSE PLANT NAMED 'DEVSMOOTH'

[75] Inventors: Stanley G. Marciel; Jeanne A. Marciel, both of Aptos, Calif.

[73] Assignee: DeVor Nurseries, Inc., Watsonville, Calif.

[21] Appl. No.: 08/873,660

[22] Filed: Jun. 12, 1997

[51] Int. Cl.[7] ..... A01H 5/00

[52] U.S. Cl. ..... Plt./150

[58] Field of Search ..... Plt./28, 29, 149–151, Plt./108

*Primary Examiner*—Howard J. Locker

*Attorney, Agent, or Firm*—Christie, Parker & Hale, LLP

[57] ABSTRACT

A floribunda rose variety producing red flowers.

1 Drawing Sheet

BACKGROUND OF THE INVENTION

The present invention relates to a new and distinct floribunda rose variety which was originated by our crossing as seed parent the variety known as 'Sassy' (U.S. Plant Pat. No. 4,559) and as pollen parent an unnamed seedling (70270-2). The varietal denomination of this new rose is 'Devsmooth'.

SUMMARY OF THE INVENTION

Among the novel characteristics possessed by the new variety which distinguish it from its parents and all other varieties of which we are aware are its attractive, bright red flowers with long stems borne with few thorns on a bushy, vigorous plant.

Asexual reproduction by budding of the new variety as performed in Watsonville, Calif., shows that the foregoing and other distinguishing characteristics come true to form and are established and transmitted through succeeding propagations. Other known forms of asexual reproduction for roses may be also employed.

COMPARISON WITH PARENT

The new variety differs from 'Sassy' in flower size and color.

BRIEF DESCRIPTION OF ILLUSTRATION

The accompanying illustration show typical specimens of the vegetative growth and flowers of the new variety in different stages of development and depicted in color as nearly true as it is reasonably possible to make the same in a color illustration of this character.

BRIEF DESCRIPTION OF THE NEW VARIETY

Parentage: Seedling.

*Seed parent.*—'Sassy' (U.S. Plant Pat. No. 4,559).

*Pollen parent.*—Unnamed Seedling (70270-2).

Class: Floribunda.

The following is a detailed description of the new variety, from specimens grown outdoors in Watsonville, Calif., in the month of September. The color terminology used is in accordance with The Royal Horticultural Society Colour Chart (R.H.S.C.C.), and refers to plate numbers in the aforementioned color chart. Phenotypic expression may vary depending on light, environmental and cultural conditions.

FLOWER

Blooming habit: Continuous.

A. Bud:

(1) *Size.*—Small, about 2 to 3 cm after sepals fall.

(2) *Form.*—Pointed.

(3) *Color.*—When sepals first divide, bud color is near 59A to 46A.

(4) *Sepals.*—Some foliaceous, about 2.5 cm long. Color: Near 144A.

(5) *Peduncle.*—Length: About 9 cm to about 11 cm. Aspect: Smooth. Strength: Erect and sturdy. Color: Near 144A.

(6) *Bracts.*—None.

B. Bloom:

(1) *Size.*—Average size when fully expanded — about 7 cm to about 9 cm.

(2) *Borne.*—Singly.

(3) *Form.*—Imbricated, cupped, petals reflex to point or curl under.

(4) *Petalage.*—Number of petals under normal conditions — about 23 to 25.

(5) *Color* (⅓–½ *open*).—Outer petals — Top surface: Near 45A but brighter. Undersurface: Near 45A. Inner petals — Top surface: Near 45B. Undersurface Near 45A. Base of petals: Near 6C. General tonality from a distance: Bright Red.

(6) *Color* (*Fully open*).—Outer petals — Top surface: Near 45A but brighter. Undersurface: Near 53B. Inner petals — Top surface: Near 45A but brighter. Undersurface Near 53B. Base of petals: Near 6C. General tonality from a distance: Bright Red.

(7) *Color change.*—Bloom stays a constant bright red; Petal top surface — Near 45A but brighter. Petal undersurface — Near 53B. General tonality: Base of petals: Near 6C. at a distance: Bright Red.

Petals:

(1) *Texture.*—Thick, smooth.

(2) *Appearance.*—Inside velvety and outside semi-satiny.

(3) *Form.*—Orbicular with slight ruffling at edges.

(4) *Arrangement.*—Imbricated.

(5) *Petaloids.*—Full, about 3 to 4.

(6) *Persistence.*—Petals drop off cleanly.

(7) *Fragrance.*—Slight fruity fragrance.

(7) *Lasting quality.*—On plant about 14 to 18 days; about 12 to 14 days after cutting.

REPRODUCTIVE ORGANS

A. Stamens:

(1) *Arrangement.*—Regularly arranged around styles.

(2) *Anthers.*—Color — near 22A.
(3) *Filaments.*—Color — near 185B.
(4) *Pollen.*—Color — near 22A.

B. Pistils:
(1) *Styles.*—Bunched, even.
(2) *Stigmas.*—Color — near 11B.

C. Characteristics of hips: Not observed.

PLANT

A. Form: Upright; height about 80–90 cm, spread about 65–75 cm; stem length about 50–55 cm.
B. Growth: Vigorous.
C. Foliage: Compound 3 to 5 leaflets.
(1) *Size.*—Medium; leaflets about 8–11 cm long and about 8–9 cm wide.
(2) *Quantity.*—Abundant.
(3) *Color.*—New foliage — upper side near 146A underside near 147B with tinges of near 182B; mature foliage — upper side near 147A, underside near 147B.
(4) *Shape.*—Oval.
(5) *Texture.*—Upper side leathery, semi-glossy; underside leathery, veiny.
(6) *Edge.*—Serrate.
(7) *Serration.*—Denticulate.
(8) *Leaf stem.*—Color — dark green.
(9) *Stipules.*—Parallel, medium length, adnate bearded, curving downward.
(10) *Rachis.*—Smooth, with occasional small prickles.
(11) *Petioles.*—Top near 147B with tinges of near 184A on edges; underside near 146C.
(12) *Auricle.*—Narrow, bearded, curving downward.
(13) *Resistance to disease.*—Very resistant to mildew, rust and blackspot.

D. Wood:
(1) *New wood.*—Color near 146A with slight tinge of near 182A, bark smooth.
(2) *Old wood.*—Color near 146A, bark smooth.

E. Flower stem: Long.
F. Thorns:
(1) *Thorns.*—Quantity: Few, very few prickles on rachis.

G. Winter hardiness: Winter hardy in Watsonville, Calif.

We claim:

1. A new and distinct floribunda rose plant of the variety, substantially as shown and described.

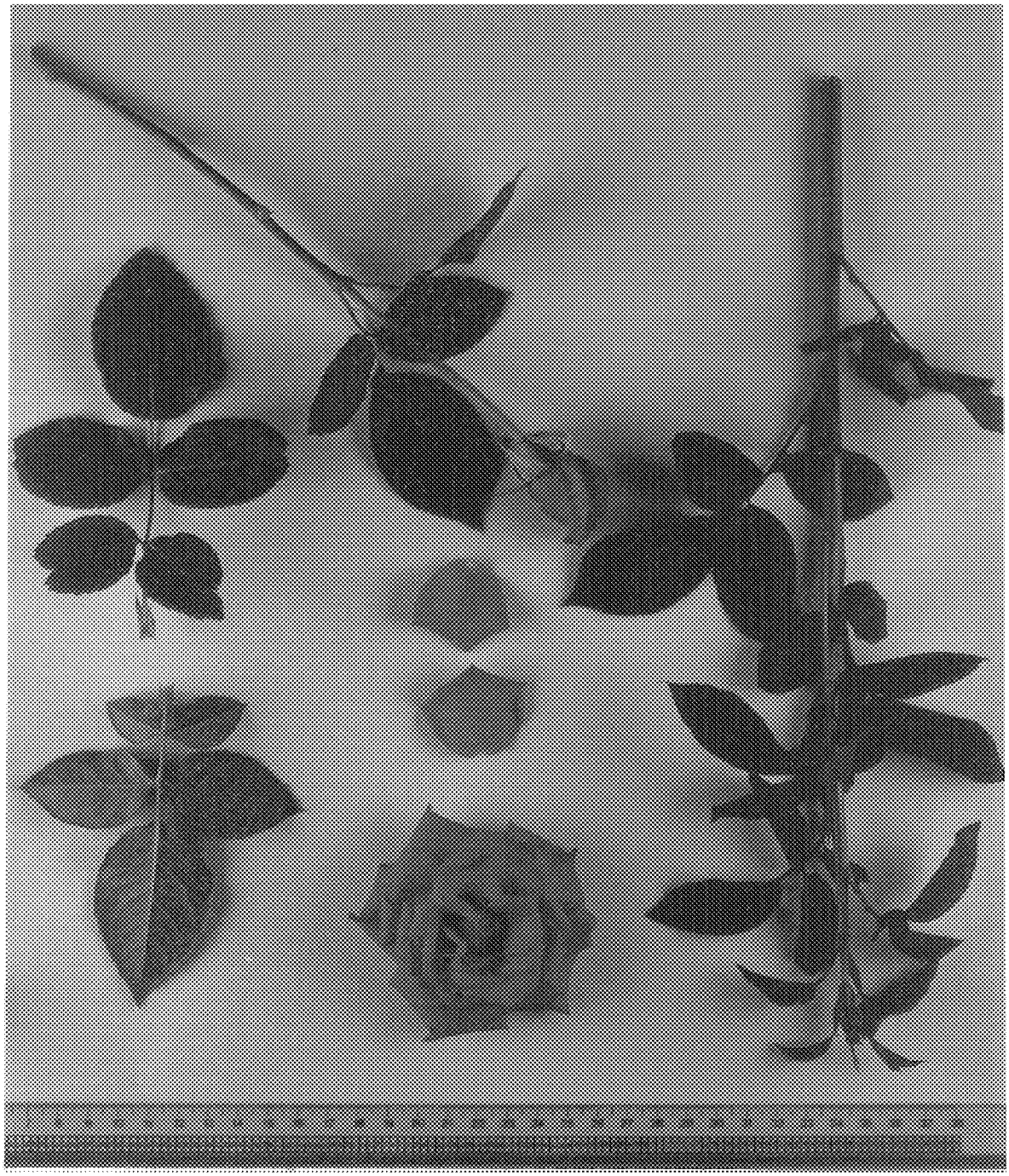

* * * * *